United States Patent [19]

Rudel

[11] 4,300,544
[45] Nov. 17, 1981

[54] DISPOSABLE FEMALE CONTRACEPTIVE

[75] Inventor: Harry W. Rudel, Mexico, Mexico

[73] Assignee: Dia-Sert Corp., White Plains, N.Y.

[21] Appl. No.: 38,725

[22] Filed: May 14, 1979

Related U.S. Application Data

[63] Continuation-in-part of Ser. No. 939,332, Sep. 5, 1978, abandoned, which is a continuation-in-part of Ser. No. 852,824, Nov. 18, 1977, abandoned.

[51] Int. Cl.³ .............................................. A61F 5/46
[52] U.S. Cl. ................................................... 128/127
[58] Field of Search ..................... 128/127, 131–132, 128/138 R, 270, 285

[56] References Cited

U.S. PATENT DOCUMENTS

| | | | |
|---|---|---|---|
| 3,128,767 | 4/1964 | Nolan | 128/285 |
| 3,216,422 | 11/1965 | Steiger et al. | 128/285 |
| 3,952,737 | 4/1976 | Liffert et al. | 128/127 |
| 3,983,874 | 10/1976 | Davis et al. | 128/285 |

FOREIGN PATENT DOCUMENTS

| | | | |
|---|---|---|---|
| 380262 | 9/1923 | Fed. Rep. of Germany | 128/127 |
| 574471 | 7/1933 | Fed. Rep. of Germany | 128/127 |
| 822877 | 11/1951 | Fed. Rep. of Germany | 128/127 |
| 366735 | 8/1906 | France | 128/127 |

*Primary Examiner*—C. Fred Rosenbaum
*Attorney, Agent, or Firm*—Philip Furgang

[57] ABSTRACT

Disclosed is a disposable contraceptive in which a first member engages the vaginal vault and a second member, secured to the first member, engages and closes the cervical opening. The first and second members are substantially discoid, with the second member smaller in discoid area than the first. The second member is a generally impermeable sponge-like material which is lubricated to aid in adhesion and closure of the cervix. The first member is generally resiliently closable so that the overall dimension of the contraceptive may be reduced in size for insertion into the vaginal vault. The first member is defined at least by opposed anterior and posterior portions which engage the respective anterior and posterior portions of the vaginal vault. The second member is coupled or joined to the first member at the posterior portion.

In one embodiment, the second member is a sponge joined to a film. The film is held in position to define the first discoid member surface by a rim.

In other embodiments, the first and second members are resiliently joined at the posterior portion so as to urge the second member into positive engagement with the cervix. Thus, a finite resilient nylon filament is bent into a figure 8 and covered with a soft, yieldable, foam plastic covering. By folding at the intersection of the upper and lower loops, the contraceptive is formed. In another example, a liner of resilient plastic in the shape of conjoined circles is covered by a soft, flexible, plastic envelope. In yet another example, an annular discontinuous rim is covered by a foam plastic. The rim has an integrally formed tongue extending therein and about, to which may be secured (by any well known means) a sponge-like impermeable plastic second member.

92 Claims, 22 Drawing Figures

DISPOSABLE FEMALE CONTRACEPTIVE

CROSS REFERENCE TO PRIOR APPLICATIONS

This application is a continuation-in-part of application Ser. No. 939,332, filed on Sept. 5, 1978, now abandoned, which was, in turn, a continuation-in-part of application Ser. No. 852,824, filed on Nov. 18, 1977, now abandoned.

BACKGROUND OF THE INVENTION

This invention relates to contraceptives and, more particularly, to a female contraceptive.

The most common type of female contraceptive is the diaphragm. A diaphragm is a device usually made of thin, flexible material which is placed in the vaginal vault for blocking the entrance to the cervix in order to prevent impregnation during sexual intercourse. Generally, such diaphragms comprise a loose hanging pouch made of an elastomeric material such as rubber formed with an integral, heavy, resilient rim intended to engage the walls of the vaginal vault. In order to prevent the intrusion of spermatozoa or disease-carrying organisms into the cervix, a diaphragm is most usually used in combination with a spermicidal cream. The combination of the two—diaphragm and the spermicidal cream—usually makes a cumbersome and inconvenient contraceptive.

Over the years, a number of improvements in contraceptives have been suggested. Thus, for example, J. T. Clark, in U.S. Pat. Nos. 2,463,356; 2,540,932; and 2,638,896; as well as Ballard et al., in U.S. Pat. No. 2,529,363; Snell, in U.S. Pat. Nos. 2,538,478; and 3,117,573; Young, in U.S. Pat. No. 2,625,154; Kunnas, Jr., in U.S. Pat. No. 2,823,669; Milgrom et al., in U.S. Pat. No. 3,036,570; Lay, in U.S. Pat. No. 2,249,316; and Duncan, in U.S. Pat. No. 3,545,439 all suggest spring-loaded diaphragm rims for resiliently collapsing the diaphragm for ease of insertion and the subsequent firm engagement of the walls of the vaginal vault.

The disadvantage of these devices is that the prophylactic effect is achieved by sealing the diaphragm at the vaginal wall. Pressure can, in some instances, result in discomfort. Insufficient pressure can result in either impregnation and/or disease entering the cervix.

Another approach was suggested by Harris in U.S. Pat. No. 2,522,822, in which a disposable vaginal diaphragm or pessary is suggested. Essentially, Harris suggests the use of a soft and pliable contraceptive. However, it is believed that such a device cannot be held securely in place within the vaginal vault, thereby causing great difficulty and possible misplacement during sexual intercourse.

Sponges or sponge-like devices have been suggested in the form of pessaries, as disclosed by Steiger et al., in U.S. Pat. No. 3,216,422; Young, in U.S. Pat. No. 3,128,762; and Cruickshank, in U.S. Pat. No. 2,020,107. In the device disclosed by Steiger et al., the sponge hangs loosely from an impervious film. The other sponge-like devices are either intended to engage the cervix in a glove-like arrangement or in a cup-like arrangement, similar in shape to prior art diaphragms. The spacing from the cervix opening of cup-like devices increases the possibility of impregnation or infection. The glove-like devices are believed to be difficult to insert and must be specially fitted to each individual user. Thus, these devices have the same disadvantages as other rim-securing diaphragm devices.

The above-referenced devices are representative of the wide variety of constructions, each having in common the fact that either the rim of the diaphragm is spring-loaded to form a specific contact and that the sealing characteristics are being provided by the rim, or a sponge-like material, which is loosely folded as such, the latter having the difficulty of being easily misplaced or mislocated in insertion.

SUMMARY OF THE INVENTION

In view of the foregoing, it is an object of this invention to provide a diaphragm which does not depend on the sealing characteristics of the rim for prophylaxis.

It is a further object of this invention to provide a female contraceptive which may be disposable.

It is still another object of this invention to provide a means for placing a member over, and thereby closing, the entrance of the cervix.

It is yet a further object of this device to provide a contraceptive which is simple in construction, economical in manufacture, and convenient to use.

In accordance with the teachings of this invention, there is provided a barrier contraceptive of the type intended to be inserted within the vaginal vault. The contraceptive comprises a first member. This first member is characterized by opposed anterior and posterior portions for alignment with respective anterior and posterior portions of the vaginal vault. A second member is coupled to the first member substantially at the posterior portion so as to engage and close the opening of the cervix upon insertion into the vaginal vault. The second member is disposed between the first member and the cervix upon insertion.

In a further aspect of this invention, there is provided a barrier contraceptive of the type intended to be inserted in a vaginal vault. This contraceptive includes a cervix engaging means. Resilient and flexible means are provided for positioning and retaining the cervix engaging means within the vault and holding the cervix engaging means in contact with the entrance to the cervix to thereby form an impermeable barrier to the cervix.

In still another aspect of this invention, there is formed a contraceptive by the process of providing a member so dimensioned as to engage the wall of a vaginal vault. The first member is defined at least by a posterior and diametrically opposed anterior portion. The process further includes the providing of a second member. The process further includes positioning the second member at the posterior portion of the first member and coupling the second member to the first member, at least substantially along the posterior portion such that, upon insertion of the contraceptive into the vaginal cavity, the second member comes into intimate contact with, and closes, the cervical portal and the first member engages the vaginal vault wall to hold the contraceptive in place.

DESCRIPTION OF THE PREFERRED EMBODIMENTS

The contraceptive 10 (FIGS. 1-3) generally comprises an annular flexible and resilient member or rim 12. The rim 12 may have a generally circular shape. It will be noted, however, that the circle is discontinuous. Preferably, this rim 12 may be made of any convenient material such as plastic, which may be, for example, a polyethylene, polypropylene, polyvinylchloride, or the like. In order to encourage the flexibility and resiliency, the posterior portion 14 of the rim 12 may be thickened. This thickened posterior portion 14 may be opposite the anterior rim opening 16. Preferably, the anterior opening 16 should be no more than ten to twenty-five percent of the circumference of the rim 12. In one example, the plastic rim may have a thickness in the range of approximately 1 to 2 mm. at the posterior portion 14, as compared to a thickness of approximately 0.5 to 1 mm. at the anterior portion 16.

Figures 1, 2, 3:
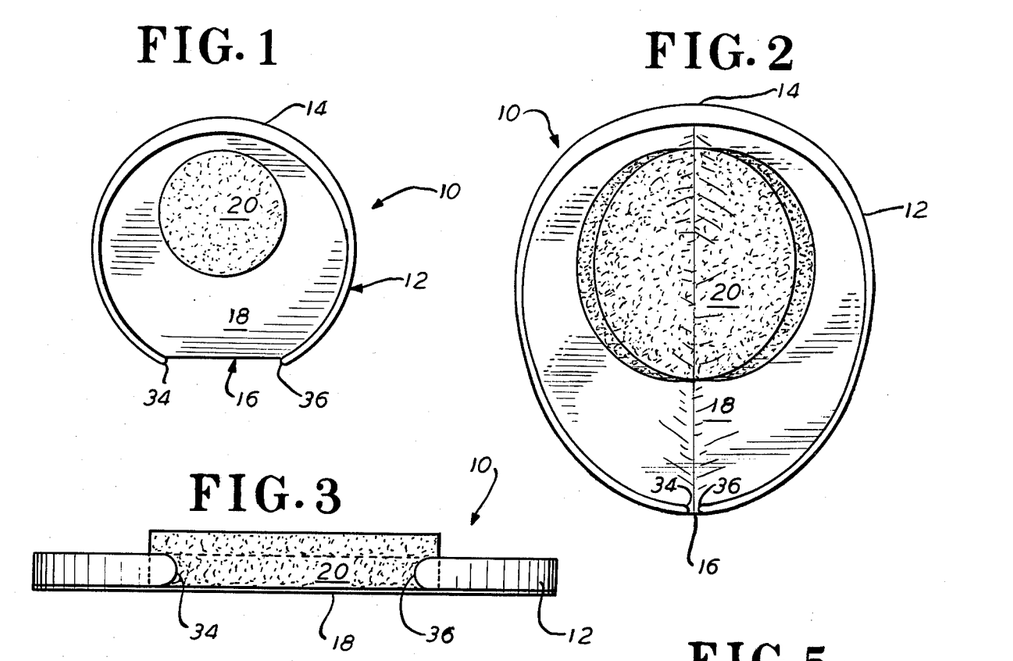
FIG. 1 is a top plan view of a disposable vaginal contraceptive constructed in accordance with the teachings of the invention.
FIG. 2 is a top plan view of the vaginal contraceptive of FIG. 1 with the ends of the ring closed.
FIG. 3 is a side view of the contraceptive of FIG. 1.

A film 18 of a flexible material, such as a plastic sheet, may be secured to the rim 12 and lie substantially in a plane. The film 18 is, preferably, made of the same plastic material as the rim 12. By using such a common material, the film 18 may be secured to the rim 12 by heat sealing methods which are well known in the art. In the alternative, the film 18 may be secured by an adhesive. It is not essential that the film 18 be connected at every point along the rim 12. This is a significant departure from prior art contraceptives, which regard as essential the integrity of the rim as attached to the remainder of the diaphragm. The film 18 may have an overall thickness of from approximately 0.125 to 1.25 mm. and, preferably, from approximately 0.38 to 0.76 mm. The thickness of the film 18 depends upon the nature of the material and its ability to be flexible. The rim 12 may have a height above the film 18 of, for example, from approximately 1 to 2.5 mm.

Attached to the film membrane 18 is a closed network of approximately material in the form of a sponge 20, preferably made of a plastic material such as polyethylene, polyurethane foam, or the like. The sponge 20 may be secured to the film 18 by heat or any other well known means of joining. The sponge 20 should be resilient and compliant. It may have, preferably, a circular outline and be discoid in shape. Its thickness may be determined by the spongy network. The minimum thickness must be such as to prevent an open passageway from the disc 20 top to bottom. Preferably, the sponge 20 may be from 2 to 5 mm. thick and have a diameter of 40 mm. The sponge 20 may be attached to the membrane very close to the posterior portion 14 of the rim 12, for reasons that will be more fully set out below.

Figure 5:
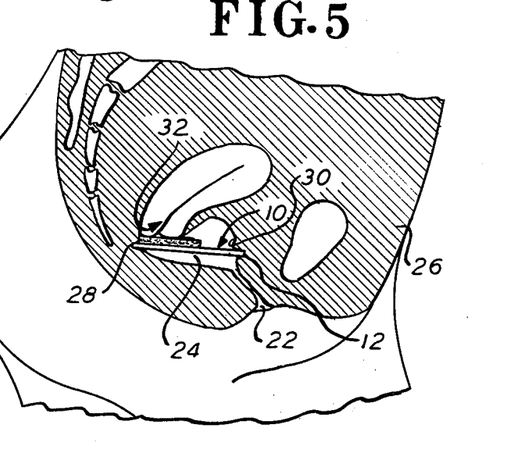
FIG. 5 is a sectional view of a female anatomy showing the vaginal vault with the contraception of FIG. 1 inserted therein.

In use, the rim 12 of the diaphragm 10 is closed (FIG. 2), thereby reducing the overall diameter and circumference. As a consequence, the film 18 and sponge 20 may be expected to buckle or bevel slightly (not visible). The diaphragm 10 may then be conveniently inserted through the vagina 22 and into the vaginal vault 24 of a female 26 (FIG. 5). Upon insertion, the diaphragm 10 may be positioned with the posterior portion 14 seated in the posterior cul-de-sac 28 of the vaginal vault 24, and the anterior open portion 16 of the diaphragm 10 may be positioned anterially toward the symphesis pubis 30. By being so positioned, the sponge 20 is disposed over and against the entrance to the cervix 32. Thus, it is the sponge 20, and not the remainder of the device 10, which acts as a barrier contraceptive. For this reason, an imperfection in the film 18 or rim 12, which admits such foreign elements as a virus, bacterium, or spermatozoon, is not critical. This enables the contraceptive to be made inexpensively and simply compared to prior art devices.

The sponge 20 may be saturated with any lubricant, such as a water-washable cream, which acts to seal the sponge 20 to the entrance of the cervix 32. The cream may be buffered to a desired pH and may carry active ingredients such as spermicides, virucides, antibiotics, or germicides.

Insertion is aided because the natural tendency of the user would be to insert the posterior portion 14 of the diaphragm 10 first. If this was not done, the anterior portion 16 might tend to open.

The overall size of the diaphragm 10 is determined by the respective size of the vaginal vault of a particular user.

In the overall configuration of the rim 18 of the diaphragm 10, the anterior opening 16 is, preferably, no more than approximately 10 to 35 percent of the circumference. The cord at its opening may be, approximately preferably, 86.39 mm. It is important that the open edges 34 and 36 of the rim 12 be rounded so as not to be abrasive to the vaginal lining.

After it has been used, the contraceptive 10 may be removed in a manner similar to other contraceptives. By virtue of its construction of inexpensive materials, the contraceptive 10 can be disposed of and a new contraceptive used on the next occasion.

An alternate rim design may be used. Thus, the rim 38 (FIG. 4) may have a helical arrangement with the ends 40 and 42 overlapping. In addition, it may prove desirable to have a flap of the film 18 formed so as to extend beyond the rim 12 at the anterior portion 16 and wrapped about the ends 34 and 36 of the first (or second) embodiment to further shield the anterior portion 16 and aid in preventing abrasion.

Still another alternative may be to dispose the sponge to extend through a convenient aperture in the film so as to easily engage the cervix, no matter which side of the device is oriented toward the cervix.

This contraceptive may be mass produced for use by most females where the location of the cervix in the vaginal vault is predictable. Thus, the appropriate size is a determination which should, preferably, be made by the individual's physician, as with any other diaphragm. The diaphragm 10 may be sized to fit. For example, a large diaphragm might have an outer diameter of approximately 110 mm. and a circumference of approximately 345.58 mm. In its closed position, with the anterior ends 34 and 36 of the rim 12 brought together, it may have an approximate diameter approximately of 82.5 mm. and a circumference of approximately 260 mm. In a medium size, it may have an open outer diameter of approximately 90 mm. and a circumference of approximately 282.74 mm., and a closed diameter of approximately 72 mm. and a circumference of approximately 226.91 mm. In a small size, the diaphragm 10 may have an open outer diameter of approximately 75 mm. and a circumference of approximately 235.62 mm. and, when closed, a diameter of approximately 63.18 mm. and a circumference of approximately 198.5 mm. Clearly, the choice of sizes is discretionary and other sizes may be established and are intended for use in the range of normal vaginal vaults and cervical openings. Abnormally shaped and sized vaginal vaults could be accommodated by appropriate dimensional changes in the contraceptive.

Figure 4:
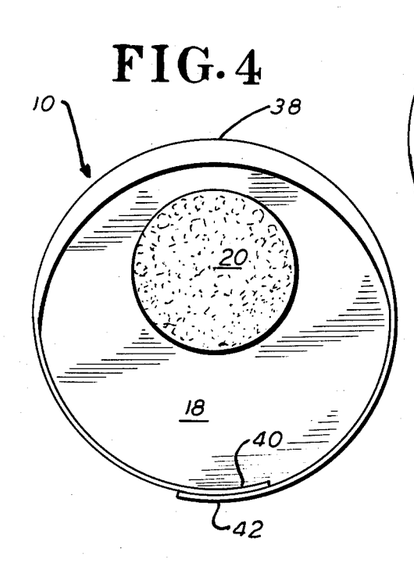
FIG. 4 is a top plan view of another embodiment of the vaginal contraceptive constructed in accordance with the teachings of this invention.
Figure 7:
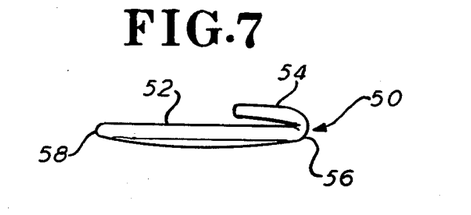
FIG. 7 is a side view of an assembled contraceptive using the filament of FIG. 6.
Figures 8, 9, 10, 11, 12:
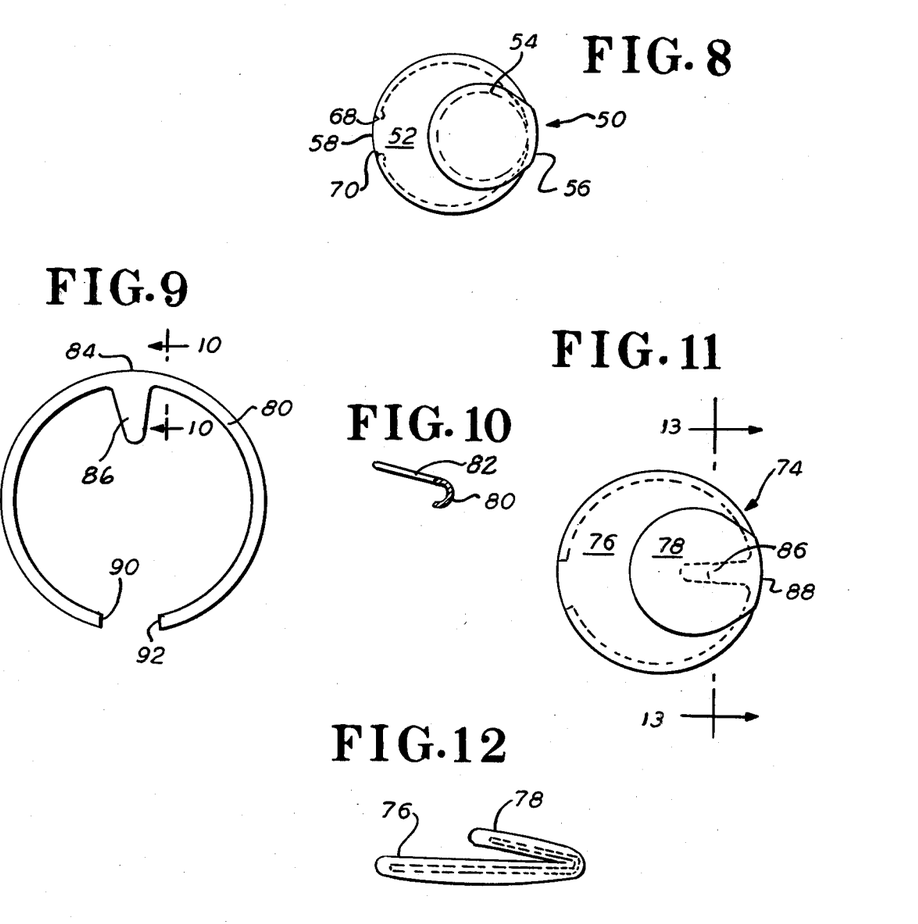
FIG. 8 is a top plan view of a vaginal contraceptive shown in side view in FIG. 7.
FIG. 9 is a top plan view of a rim used in still another embodiment of a vaginal contraceptive constructed in accordance with the teachings of the invention.
FIG. 10 is a sectional view of the rim of FIG. 9, taken along the lines 10—10.
FIG. 11 is a top plan view of a vaginal contraceptive employing the rim of FIG. 9.
FIG. 12 is a side view of the contraceptive of FIG. 11.

Turning to another embodiment, there is disclosed, in FIGS. 7 and 8, another contraceptive 50 which is similar in many respects to the devices disclosed in FIGS. 1 and 4. There are provided two generally discoid-shaped members 52 and 54. The larger of the two discoid members 52 may have the same general disc edge dimensions as that defined by the rim 12. This marginal edge of this first discoid member 52 is defined by posterior and anterior portions 56 and 58, respectively. The second substantially discoid member 54 is coupled to the first discoid member 52 substantially at the posterior portion 56 and has substantially the same overall dimensions as the second discoid member 20 or sponge 20 of the devices disclosed in FIGS. 1 and 4.

This contraceptive 50 has, however, certain features which distinguish it from the previously discussed contraceptives (FIGS. 1 and 4). The present contraceptive 50 comprises a filament 60, which may be made of any resilient material such as, for example, nylon thread. It will be noted that the filament 60 (FIG. 6) is twisted into a figure 8 configuration, with the upper loop 62 being substantially smaller than the lower loop 64. The natural tendency of the filament 60 is to form two substantially ellipsoid portions 62 and 64. The upper loop may have, for example, a dimension of approximately 38.1 mm. by 31.8 mm. with the major axis intersecting the intersection 66 of the cross filament 60. The lower and larger ellipsoid may have a dimension of, for example, approximately 66.7 mm. by 63.5 mm. with the major axis running perpendicularly to the major axis of the upper loop 62. The above dimensions are, by way of example, of the ratio of sizes of the upper discoid loop 62 to the lower discoid loop 64. In actual use, dimensions of larger and smaller discoids 64 and 62, respectively, will be as discussed in connection with the devices of FIGS. 1 and 4.

Figure 6:
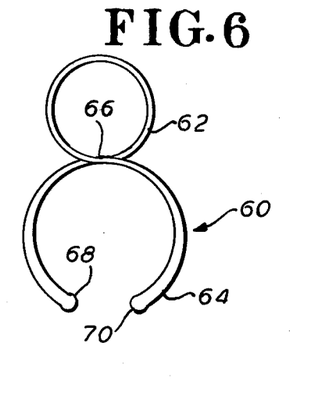
FIG. 6 is a top plan view of a filament used in another embodiment of a vaginal contraceptive constructed in accordance with the teachings of this invention.

The filament 60 may have a diameter of approximately 0.25 to 2 mm. and, preferably, approximately 0.5 mm. thick.

To complete the contraceptive 50, the filament 60 may be covered or enveloped by any well known plastic material such as, for example, a polyethylene film of approximately 1 to 3 mm. in thickness, which is heat sealed at the edges. The double film, which may also be made of a sponge-like construction, provides the discoid surfaces 52 and 54 with a texture approaching that of human skin. It will be noted that both ends of the filament 60 terminate in the first discoid member 52. These open ends 68 and 70 of the filament 60 may be rounded so as to prevent a sharp discontinuous edge. In assembly, the second discoid element 54 is folded over the first discoid element 52. The natural "memory" resiliencey of the filament 60 causes or tends to cause the second discoid member 54 to move resiliently upwardly and away from the first discoid member 52. This "memory" factor of the filment 60 serves to push the upper discoid 54 in the direction of the cervix 32 (FIG. 5). Thus, this embodiment, like all others herein, has in common the separation of the function of the contraceptive into two distinct parts: one, the lower and larger discoid member, positions the contraceptive and engages the vaginal cavity. Secondly, the upper contraceptive member closes or seals shut the cervical opening or portal. The open ends 68 and 70 of the filament 60 enable the closing thereof so that the larger discoid 52 of the contraceptive 50 may be domed or formed into a concavity for insertion into the vaginal vault.

Turning to yet another embodiment (FIGS. 9 through 13), there is disclosed a contraceptive 74 comprised of a larger first discoid member 76 and a smaller-dimensioned second discoid member 78 (FIG. 11). The contraceptive 74 is formed by means of an annular rim 80 (FIG. 9). The rim 80 may be made of polymerized plastic and may have a generally concave semicircular cross-section (FIG. 10). Thus, the overall rim 80 may be approximately 1 mm. thick and have a substantially semicircular cross-section with an outer diameter of approximately 2 mm. Integrally formed, and also approximately 1 mm. of thickness and extending at the upper edge 82 of the rim 80 and at the posterior portion 84, may a tongue 86. The tongue 86 may extend inwardly of the rim 80 for approximately 30 to 50 mm. and have a width of approximately 4 to 6 mm. The tongue 86 may be provided with a slight cant upward from the plain defined by the upper edge 82 of the rim 80. The function of this cant or upward acute angle will be more fully discussed hereinafter.

Figure 13:
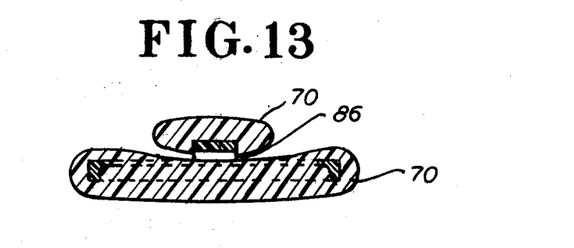
FIG. 13 is a sectional view of the vaginal contraceptive of FIG. 11, taken along line 13.

In order to construct the contraceptive 74 of this embodiment, it may be preferable to place the rim 80 in a mold having a substantially dish-like cavity (not shown). A polymerizable plastic may then be foamed about the rim so as to cover the rim 80 and leave exposed the tongue 86. This polymerized portion forms the lower or larger first discoid member 76 (FIG. 13). As a second step, a shim or other molding device may be placed between the first member 76 and the tongue 86. The second discoid member 78 may then be foamed in situ on top of the shim (not shown) to thereby form the second discoid member 78. The second discoid member 78, as in the prior embodiments, is located substantially at the posterior portion 88 of the first discoid member 76.

It will be noted that the rim 80 is open at its ends 90 and 92 to permit, as with the other devices herein, the doming of the contraceptive 74 for ease of insertion into the vaginal vault 24. It will be noted that the first discoid member 76 has a somewhat concave cross-section (FIG. 13) so as to encourage the collapse of the contraceptive 74 and aid in the insertion into the vaginal vault 24 and to further encourage the lifting of the cervical cover, or second discoid member, 78. This second discoid member 78 may have a thickness of approximately 3 to 4 mm.

Still another embodiment is a contraceptive 96 (FIGS. 14 through 17), in which the "memory" of a plastic material is employed. A linear 98 (FIG. 14) of a "memory" plastic, or like material, may be employed. Such a material, for example, may be a polyethylene rigid foam with a closed cellular network having, for example, an approximate thickness of 1 to 4 mm. In this instance, the liner 98 may have a "snowman" shape defined by a discoid first member 100 which is, preferably, substantially circular and surmounted by an integrally formed circular second discoid 102 portion. The "memory" aspect of this material is such that when the second discoid member 102 is folded over the first discoid member 100 at the junction of the two circular portions 104, the liner 98 straightens out, or returns, to a planar position.

Figure 14:
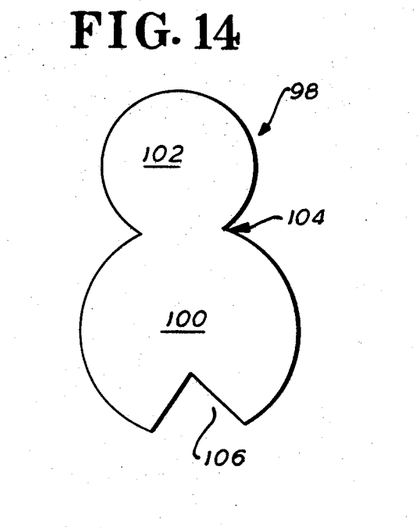
FIG. 14 is a top view of a member used in the construction of yet another embodiment of a vaginal contraceptive constructed in accordance with the teachings of this invention.

The second discoid member 102 may be, for example, approximately 35 to 40 mm., while the lower or first discoid 100 may have a diameter of approximately 60 to 75 mm.

The cord formed at the juncture 104 of the two circular, or discoid, portions 100 and 102, may have a length of approximately 15 to 20 mm. in length. Obviously, the greater the overlap of the two circular configurations of the upper and lower discoids 100 and 102, the longer the cord and the greater the resiliency in the tendency of the liner 98 to return to a planar configuration.

It will be noted that there is a discontinuity, or interruption, 106 in the circumference of the first discoid member 100. This discontinuity 106 may be in the form of a segment of the circle, providing an angular opening of between approximately 90° and 110°, of which a cord may be defined of about 25 to 30 mm. in length. This discontinuity 106 is to aid in the folding of the contraceptive 96 and the doming thereof for ease of insertion into the vaginal vault.

Figure 15:
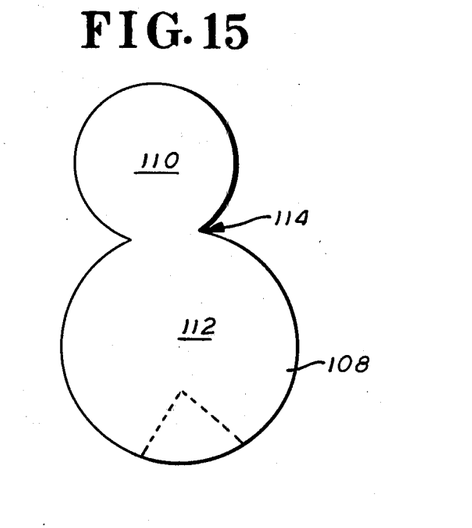
FIG. 15 is a top view of a contraceptive using the member of FIG. 14.
Figure 16:
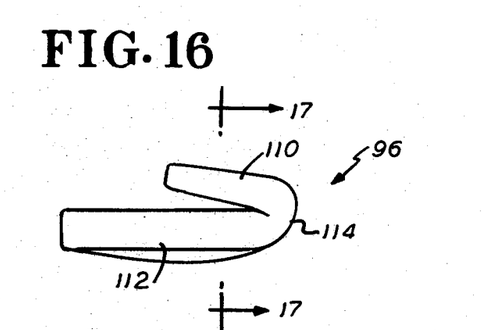
FIG. 16 is a side view of an assembled contraceptive of the device of FIG. 15.
Figure 17:
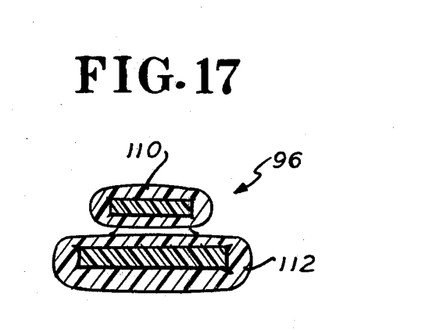
FIG. 17 is a sectional view of the vaginal contraceptive of FIG. 16, taken along line 17.

The rigid liner 98 may be covered by a soft, cellular, easily deformable plastic covering 108 (FIGS. 15 through 17). The combined soft cellular covering 108 has the same general configuration as the more resilient and relatively more rigid liner 98. The combination thereby forms the contraceptive 96. The covering 108 may be joined by heat sealing or the like to thereby define the first and second discoid members 112 and 110, respectively.

In assembly, the contraceptive 96 is formed by folding the second discoid member 110 over the first discoid member 112 (FIGS. 16 and 17). Upon insertion into the vaginal vault 24, the discontinuity 106 of the first discoid portion 100 is closed, causing the contraceptive 96 to dome or form a concavity in the first member 112. This has the effect of reducing the diameter of the contraceptive 96 to aid insertion into the vaginal vault 24 and to cause or aid the tendency of the second member 110 to move upwardly and away from the first member 112 and in compliance with the "memory" of the liner 98.

As with the previously discussed devices herein, 10 (FIGS. 1 and 4), 50 (FIGS. 7 and 8), and 74 (FIGS. 11 and 12), the contraceptive 96 has a smaller discoid member 110 coupled substantially at the posterior portion 114 of the first discoid 112. This posterior portion 114 is coincident with the aforementioned juncture 104 of the liner 98. The disposition of the second discoid 20 (FIGS. 1 and 4), 54 (FIGS. 7 and 8), 78 (FIGS. 11 and 12), and 110 (FIGS. 16 and 17) is to come into contact with the cervical opening, closing it to germs, spermatozoa, or the like. In this connection, such a second discoid 20, 54, 78, and 110 may be moistened by any of the materials mentioned in connection with the second discoid 20 of the first two embodiments (FIGS. 1 and 4). In addition, it is believed to be desirable to use a material which aids the adherence of these second discoids 20, 54, 78, and 110 to the cervix, such as by use of, for example, a tenacious gel employing a gum adhesive property. Such adhesives may be, for example, guar, tragacanth, caragenin, or the like.

While the embodiments herein have certain structural characteristics in common, there are some distinguishing characteristics, as well.

The sponge 20 of the embodiments of FIGS. 1 and 4 is disposed against the cervical opening by the first discoid member, or film, 18. In the remaining embodiments of FIGS. 7, 8, 11, 12, 16, and 17, the second discoid members 54, 78, and 110 are resiliently movable with respect to the first discoid members 52, 76, and 112, respectively. Thus, when each of these latter devices is inserted into the vaginal vault, the resiliency or tendency of the second members 54, 78, and 110 to open into a co-planar relationship to the respective first discoid members 52, 76, and 112 is employed to cause greater contact pressure of the second discoid members 54, 78, and 110 with the cervical opening.

The overall dimensions of each discoid member are, preferably, in accordance with those set forth in connection with the first disclosed embodiment (FIG. 1).

It should be noted that the term "discoid" is used throughout as a matter of convenience, and any desired shape may be employed, such as elliptical or oval, as long as the closing of the cervical opening by the second member and the holding in position by the first member is accomplished.

In each instance, the second member of each embodiment herein is made of an impermeable sponge-like material which has been lubricated with any or all of the substances heretofore mentioned.

In each of the embodiments herein, it will be noted that the first discoid member is characterized by an interruption or discontinuity in the circumference at the anterior portion. This discontinuity may be from approximately 33⅓ to 15 percent of the circumferential length and preferably approximately 25 percent of the circumference of the discoid. It is well known that there are many different sized vaginal vaults. In the prior art, it has been necessary to "size" a contraceptive to fit a particular vaginal vault. The design of the circumference of the first member of this invention enables the contraceptive to be self-adjusting to a great many differently sized vaginal vaults. Thus, one contraceptive may fit many different dimensioned vaults. In this way, the design of the first member is applicable to other female contraceptives independent of the other features of this invention.

The adjustability of the contraceptive is to be distinguished from prior art devices in which spring-loaded rims are closeable. In each such device, it is believed that the sole purpose is to promote compliance of a "sized" contraceptive to irregularities in the vaginal wall.

In a further embodiment, there is provided a contraceptive 120 (FIGS. 18 through 22) in which the "memory" of a plastic material is employed. This contraceptive 120 is characterized by a general "snowman" shape, similar to that disclosed in FIGS. 14 through 17. The outer marginal edge 121 of the contraceptive 120 defines two conjoined discoid members 122 and 124 interconnected at a common chord 126. The line of juncture 126 defines the posterior portion 126 of the larger discoid member 122.

Figure 19:
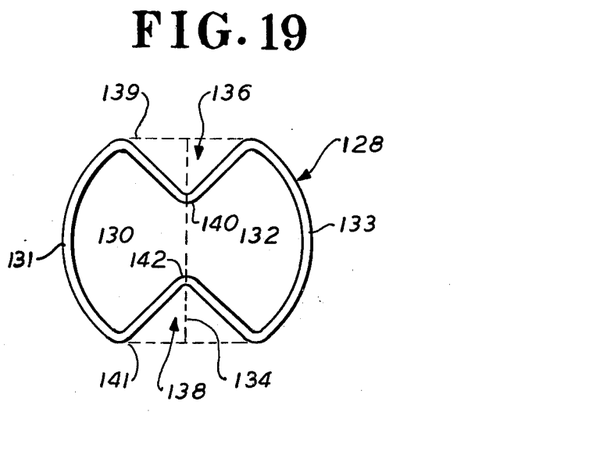
FIG. 19 is a top view of a rim constructed in accordance with the teachings of this invention.
Figure 20:
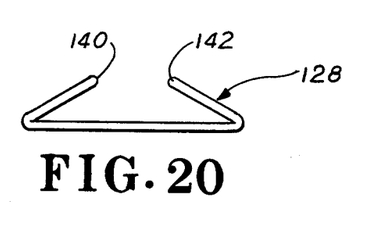
FIG. 20 is a side view of the rim of FIG. 19.

As with the previously described devices, the larger member 122 is intended to engage a vaginal vault. Within this member 122 is a rim 128 (FIGS. 19 and 20). The rim 128 may be broadly defined as being generally annular and more particularly defined by two conjoined partial obtuse segments 130 and 132. The portions 131 and 133 of the rim 128 obtuse partial segments 130 and 132, respectively, define a part of a circumference of a circle. The partial obtuse segments 130 and 132 meet at an imaginary line 134. Opposed acute angles 136 and 138 are thereby defined by the juncture of the two partial obtuse segments 130 and 132. The apexes 140 and 142 of these acute angles 136 and 138, respectively, intersect the line 134 and are spaced from one another. The rim 138 may then be covered or enclosed in a discoid-shaped envelope, previously indicated in 122. This envelope 122 may be made of any polyethylene foam. The rim 128 may be made of any plastic capable of giving it a resilient, flexible memory.

Preferably, the rim may be made of a plastic having a thickness of approximately 2.7 mm. However, it may assume any thickness in a range of approximately from 2.3 to 3.00 mm. The outer circumference 131 and 133 of the obtuse segments 130 and 132 may lie within a circle having a diameter of, preferably, approximately 68 mm, but may be within a range of approximately 60 mm to 85 mm. Chords 139 and 141 defining the point between the acute angles 136 and 138 may have a preferable length of approximately 30 mm, but may be in the range of anywhere from approximately 25 mm to 40 mm. The curvature of the apexes 140 and 142 may be approximately 5 mm.

It is preferred that the apexes 140 and 142 of the rim 128 be raised above the plane defined by that portion 131 and 133 of the rim 128 defining the obtuse segments 130 and 132. Thus, preferably, the apexes 140 and 142 would extend inwardly from the circle defined by the obtuse sections 130 and 132, a distance of approximately 20 mm, but which may be within an approximate range of 15 mm to 25 mm and extend upwardly above the plane (FIG. 20) at the apexes 140 and 142 by a distance of approximately 8.5 mm and within an approximate range of 6.0 to 10.0 mm.

Figure 18:
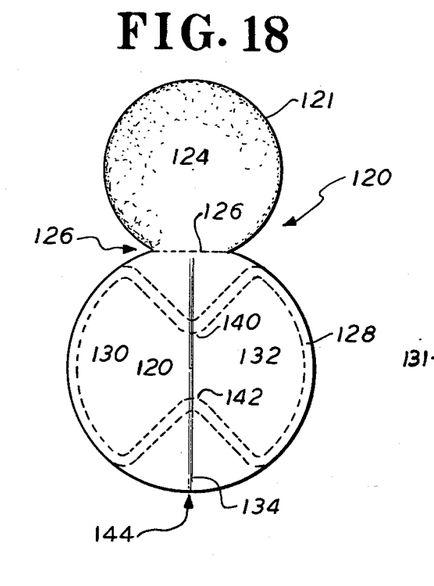
FIG. 18 is a top view of a member used in the construction of yet another embodiment of a vaginal contraceptive constructed in accordance with the teachings of this invention.

The rim 128, as indicated, may be covered by a polyethylene covering, or any similar foam plastic. Preferably, there may be two polyethylene sheets in the shape of the snowman (FIG. 18). The rim 128 may be sandwiched between the two polyethylene sheets and heat-sealed in the manner well known in the art. Preferably, each polyethylene sheet may have a thickness of approximately 3/32 to ⅛ of an inch.

Alternatively, a single sheet of polyethylene, in the shape of a snowman, may have the rim 128 disposed thereon, and a circular polyethylene sheet (not indicated) may then be placed upon the rim 128 and enclose it therein in the lower portion 122 of the diaphragm 120. In such an instance, it is preferred that the snowman portion be a piece of polyethylene foam of approximately 3/16 to ¼ of an inch in thickness, with the covering circular polyethylene sheet having a thickness of approximately 3/32 to ⅛ of an inch.

The above selected thicknesses of the polyethylene sheet are intended so that the diaphragm will be comfortably inserted into the vaginal vault of the user.

As discussed with the prior devices, the smaller discoid cervix-engaging member 124 of this invention may be lubricated, particularly with an adhesive gel. For ease of insertion, the lower member, or vaginal vault-engaging member 122, may be lubricated with a silicone lubricant.

It will be noted that the rim 128 is oriented in the lower member 122 so that the apexes 140 and 142 are co-linear with the diameter 134 which extends from the posterior portion 126 to the anterior portion 144. The raised portions of the apexes 140 and 142 provide the diaphragm 120 with a lower member 122 with a dome shape to aid in directing the insertion, as will appear more fully below.

Figure 21:
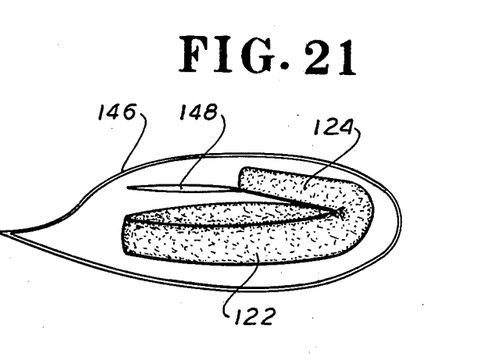
FIG. 21 is a side view of the contraceptive of FIG. 18 assembled in a package.

The diaphragm 120 may be packaged in a cellophane wrapper 146, which is heat-sealed in the usual manner. A second impermeable cellophane sheet 148 may be disposed between the cervix-engaging member 124 and the vaginal vault-engaging member 122 so that the adhesive in the upper member 124 does not come in contact with the lubricated lower member 122.

Figure 22:
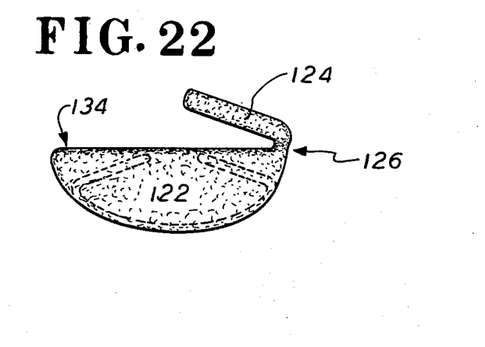
FIG. 22 is a side view of the contraceptive of this invention shown with the lateral sides folded for insertion.

In use, the lower member 122 may be folded along the diameter 134. The folding tends to move the upper member 124 upward and away from the plane defined by the discoid 122 so that, upon insertion, the cervical-engaging member 124 moves upwards to engage the cervix as the diaphragm 120 enters the anterior portion of the vaginal vault.

It is believed that a substantial advantage may be obtained by this embodiment, in that, as the sides 131 and 133 of the diaphragm open in the vaginal vault, the member 122 will engage the lateral sides of the vaginal vault. This may eliminate, therefore, the need for multiple sizes of any number of vaginal diaphragms, since the degree to which the vaginal-engaging member 122 will open will be dependent upon the resiliency of the rim 128 and the walls of the vaginal vault that it engages in. Thus, it will be seen that the sides of the rim 131 and 133 of the obtuse partial segments 130 and 132, respectively, engage the lateral walls of the vaginal vault to maintain the position of the diaphragm 120 within the vaginal vault. The preferable dome-like construction further aids in guiding the user in the proper folding of the diaphragm upon insertion, although it is not believed entirely required that the diaphragm be domed along the diameter 134.

What is claimed is:

1. A barrier contraceptive of the type intended to be inserted within a vaginal vault, said contraceptive comprising:
   (a) a first member means having opposed anterior and posterior portions for releasably and resiliently engaging the respective anterior and posterior portions of the vaginal vault; and
   (b) a second member means coupled to said first member substantially at said posterior portion, such that, upon insertion of said contraceptive into the vaginal vault, with said second member disposed beteen said first member and the cervix, and said first member posterior and anterior portions engaging, respectively, the posterior and anterior portions of the vault; said second member being positionable to thereby close the cervical openings and be substantially removed from contact with the vaginal vault such that said first member buffers said second member from the effects of the forces of the vaginal vault to thereby substantially maintain said second member in position.

2. A contraceptive as recited in claim 1 wherein said first and second members each having substantially discoid configurations and said second member having a smaller disc surface area than said first member.

3. A contraceptive as recited in claim 2 wherein said second member comprises a sponge-like material, said sponge material being capable of receiving a lubricant.

4. A contraceptive as recited in claim 3 wherein said first member comprises a substantially resilient annular member and a flexible film secured to said annular member and lying substantially in a plane; said second member being secured to said film and within said annular rim.

5. A barrier contraceptive as recited in claim 4 wherein said annular member comprises a rim having a generally circular configuration and having a discontinuous portion, so that the free ends of said rim may be pressed together, thereby reducing the diameter of said rim.

6. A contraceptive as recited in claim 5 wherein said discontinuous portion of said rim being said anterior portion and said sponge being secured to said film, substantially adjacent to said posterior portion of said rim.

7. A contraceptive as recited in claim 6 wherein said rim being thicker at said posterior portion than at said free ends to thereby improve said resiliency.

8. A contraceptive as recited in claim 7 wherein said rim, sponge, and film being each made of a plastic.

9. A contraceptive as recited in claim 8 wherein said free ends of said rim are rounded; said sponge extending higher from the plane defined by said film than said rim extends from said plane.

10. A contraceptive as recited in claim 9 wherein said posterior rim has a thickness of from approximately 1 to 2 mm., said anterior free ends of said rim have a thickness of from approximately 0.5 to 1 mm., said rim and sponge being secured to said film by heat sealing, said film being co-terminus with the outer circumference of said rim and defining a cord at said anterior portion, said sponge being from approximately 2 to 5 mm. thick, being discoid, and having a diameter of approximately 40 mm., said film having a thickness of from approximately 0.125 to 1.25 mm.

11. A contraceptive as recited in claim 6 wherein said sponge is secured to one side of said film so that said film covers one exposed surface of said sponge.

12. A contraceptive as recited in claim 6 wherein said sponge is secured to said film and having two exposed surfaces on either side of said planar surface of said film.

13. A contraceptive as recited in claim 4 wherein said annular member comprises a rim having a generally circular configuration and further comprises overlapping separate ends along said anterior portions such that, upon pressing radially upon said rim, said free ends move about said circumference of said rim to thereby reduce the diameter of said rim.

14. A contraceptive as recited in claim 6 wherein said film further comprises a flap extending from said anterior portion and without said rim being wrapped about said free ends of said rim and joined to said film within said rim.

15. A contraceptive as recited in claim 3 wherein said second member being resiliently secured to said first member for movement away from said first member so as to yieldably contact and close the cervical opening.

16. A contraceptive as recited in claim 5 further comprises a resilient and flexible filament of finite length and bent into a figure 8 to thereby exhibit a tendency to remain in a plane; said first and second members circumferential dimensions being substantially defined by said figure 8 configuration.

17. A contraceptive as recited in claim 16 further comprises a soft, pliable, sponge-like, plastic material enveloping said figure 8 filament and conforming to said shape, said second member being said upper loop of said figure 8 and said first member being said lower loop, said upper loop being folded over said lower loop at the juncture of said loops, said juncture corresponding to said posterior portion.

18. A contraceptive as recited in claim 17 wherein said filament terminates in said lower loop at said anterior portion so that said ends may be pressed together, thereby reducing the diameter of said rim.

19. A contraceptive as recited in claim 18 wherein said first and second members each being substantially ellipsoid, the major axis of said second member being perpendicular to the major axis of said first member, said major axis of second member intersecting said juncture of said loops, and said ends of said filament being rounded.

20. A contraceptive as recited in claim 19 wherein said filament is made of a plastic and has a cross-section diameter in an approximate range of 0.25 to 2 mm. and said plastic covering comprising opposed sheets, each of approximately 1 to 3 mm. in thickness, said upper loop having dimensions of approximately 38.1 mm. by 31.8 mm.

21. A contraceptive as recited in claim 15 wherein said first member comprises a substantially resilient annular member; said second member comprises a tongue integrally formed within said annular member at said posterior portion and extending inwardly of said rim.

22. A contraceptive as recited in claim 21 wherein said rim in generally circular and having a discontinuous portion opposed to said tongue so that the free ends of said rim may be pressed together to thereby reduce the diameter of said rim.

23. A contraceptive as recited in claim 22 wherein said first member further comprises a soft, sponge-like plastic covering about said rim and enclosing the space therewithin; said second member further comprises a sponge-like plastic covering secured to said tongue.

24. A contraceptive as recited in claim 23 wherein said tongue extends resiliently upwardly from the discoid plane of said first member at an acute angle.

25. A contraceptive as recited in claim 24 wherein said rim being formed from a resilient plastic of approximately 1 mm. thick and formed to define the circumference of a semicircle with an outer diameter of approximately 2 mm.; said tongue extending inwardly of said rim for approximately 30 to 50 mm. and being approximately 4 to 6 mm. wide; said second member having a thickness of approximately 3 to 4 mm. and a diameter of approximately 40 mm.

26. A contraceptive as recited in claim 15 further comprises a continuous resilient liner and an envelope of soft, flexible material; said liner tending to return to a plane; said liner and flexible material being folded along said posterior portion to thereby form said first and second members.

27. A contraceptive as recited in claim 26 wherein said liner having a notch at said anterior portion such that the ends defined by said notch may be drawn together to thereby reduce the circumferential dimension of said second member.

28. A contraceptive as recited in claim 27 wherein said liner comprises two conjoined circles, said liner and said envelope being folded along a cord defined by the juncture of said circles, said notch being a segment of said first member circle.

29. A contraceptive as recited in claim 28 wherein said second member may have a diameter of approximately 40 mm., said segment having an angle of approximately 90° to 110°, said cord defined by said juncture of said circles being approximately 15 to 20 mm. in length, said liner having a thickness of approximately 1 to 4 mm., said soft envelope being heatsealed along the circumferential edges and made of a foam, spongelike plastic of approximately 2 mm. in thickness.

30. A contraceptive as recited in claim 3 further comprises a lubricant, said second member being moistened by said lubricant to thereby aid in closing said cervical opening; said second member being impermeable.

31. A contraceptive as recited in claim 30 wherein said lubricant further comprises adhesive properties so as to thereby aid in the adhesion of said second member upon being disposed against the cervix.

32. A contraceptive as recited in claim 6 further comprises a lubricant, said second member being moistened by said lubricant to thereby aid in closing said cervix; said second member being impermeable.

33. A contraceptive as recited in claim 32 wherein said lubricant further comprises adhesive properties so as to thereby aid in the adhesion of said second member upon being disposed against the cervix.

34. A contraceptive as recited in claim 10 further comprises a lubricant, said second member being moistened by said lubricant to thereby aid in closing said cervix; said second member being impermeable.

35. A contraceptive as recited in claim 34 wherein said lubricant further comprises adhesive properties so as to thereby aid in the adhesion of said second member upon being disposed against the cervix.

36. A contraceptive as recited in claim 15 further comprises a lubricant, said second member being moistened by said lubricant to thereby aid in closing said cervix; said second member being impermeable.

37. A contraceptive as recited in claim 36 wherein said lubricant further comprises adhesive properties so as to thereby aid in the adhesion of said second member upon being disposed against the cervix.

38. A contraceptive as recited in claim 20 further comprises a lubricant, said second member being moistened by said lubricant to thereby aid in closing said cervix; said second member being impermeable.

39. A contraceptive as recited in claim 38 wherein said lubricant further comprises adhesive properties so as to thereby aid in the adhesion of said second member upon being disposed against the cervix.

40. A contraceptive as recited in claim 25, further comprising a lubricant, said second member being moistened by said lubricant, to thereby aid in closing said cervix; said second member being impermeable.

41. A contraceptive as recited in claim 40 wherein said lubricant further comprises adhesive properties so as to thereby aid in the adhesion of said second member upon being disposed against the cervix.

42. A contraceptive as recited in claim 29 further comprises a lubricant, said second member being moistened by said lubricant to thereby aid in closing said cervix; said second member being impermeable.

43. A contraceptive as recited in claim 42 wherein said lubricant further comprises adhesive properties so as to thereby aid in the adhesion of said second member upon being disposed against the cervix.

44. A contraceptive of the type intended to be inserted within a vaginal vault, said contraceptive comprising:
 (a) cervix engaging means; and
 (b) resilient and flexible means for positioning and retaining said cervix engaging means within the vault, holding said cervix engaging means in contact with the entrance to the cervix, said cervix engaging means being so dimensioned as to be substantially removed from contact with the vault such that said resilient and flexible means substantially buffers said cervix engaging means from the forces of the vaginal vault, so that said cervix engaging means forms an impermeable barrier to the cervix.

45. A contraceptive as recited in claim 44 wherein said resilient and flexible means comprises a substantially circular rim and a film of impermeable material secured to said rim; said cervix engaging means comprises a substantially impermeable sponge secured to said film.

46. A contraceptive as recited in claim 45 wherein said rim having posterior and anterior portions corresponding to and for engaging at least the posterior and anterior portions of the vaginal vault; said rim being discontinuous at said anterior portion such that, upon pressing upon said rim, said rim being resiliently reduced in size, said film flexibility yielding to said rim and returning to its original condition upon said rim being released.

47. A contraceptive as recited in claim 44 further comprises a continuous, resilient filament of finite length disposed to form upper and lower loops of a figure 8; and a soft, foam-like plastic material enveloping said figure 8, said upper loop being substantially elliptical and folded over said lower loop at the intersection of said loops, said upper loop thereby defining said cervix engaging means; said lower loop, in combination with said covering, thereby defining said resilient and flexible means.

48. A contraceptive as recited in claim 47 wherein said lower loop having posterior and anterior portions corresponding to and for engaging at least the posterior and anterior portions of the vaginal vault; said fold being at said posterior portion, the ends of said filament being spaced apart at said anterior portion such that, upon pressing said lower loop together, said lower member being resiliently reduced in size; said covering flexibly yielding to said filament; said filament resiliently urging said cervic engaging member into the plane of said resilient and engaging means.

49. A contraceptive as recited in claim 44 wherein said resilient and flexible means comprises a substantially circular rim and an envelope of soft, flexible sponge-like plastic; said cervix engaging means comprises a tongue-like extension integrally formed in said annular rim and extending inwardly thereof and a discoid-shaped sponge-like plastic member secured to said tongue.

50. A contraceptive as recited in claim 49 wherein said rim having posterior and anterior portions corresponding to and for engaging at least the posterior and anterior portions of the vaginal vault; said rim being discontinuous at said anterior portion such that, upon pressing upon said rim, said rim being resiliently reduced in size, said plastic envelope about said rim yielding to said rim and returning to its original position upon said rim being released.

51. A contraceptive as recited in claim 44 wherein said cervix engaging means, in combination with said resilient and flexible means, comprises a liner of a resilient plastic material and a soft, flexible, sponge-like plastic enveloping said liner; said cervix engaging means and flexible means being further defined by two discoid members intersecting at a common cord and folded therealong; said liner tending to resiliently urge said cervix engaging means away from said resilient and flexible means to thereby positively engage the cervix upon insertion into the vaginal vault.

52. A contraceptive as recited in claim 51 wherein said resilient and engaging means having at least anterior and posterior portions corresponding to and for engaging at least the posterior and anterior portions of the vaginal vault; said liner having a segment-like notch at the anterior portion such that, upon pressing said liner segment edges together, said resilient and engaging means being reduced in size, said covering flexibly yielding to said liner and returning to its original position upon said liner being released.

53. A contraceptive as recited in claim 46 wherein said cervix engaging member further comprises a lubricant having adhesive properties and said engaging member being impermeable.

54. A contraceptive as recited in claim 48 wherein said cervix engaging member further comprises a lubricant having adhesive properties and said engaging member being impermeable.

55. A contraceptive as recited in claim 50 wherein said cervix engaging member further comprises a lubricant having adhesive properties and said engaging member being impermeable.

56. A contraceptive as recited in claim 52 wherein said cervic engaging member further comprises a lubricant having adhesive properties and said engaging member being impermeable.

57. A female contraceptive for use in a vaginal vault and acting as a barrier for blocking the entry of foreign matter into a cervix; said contraceptive comprising:

(a) member means for providing the barrier; and
(b) rim means for engaging the wall of the vault and being in cooperative engagement with said member means; said rim means being resiliently and flexibly engageable with the vaginal vault for positioning said contraceptive and having a circumferential discontinuity so dimensioned as to permit said rim to be resiliently reduced in size so as to be accommodated by vaginal vaults of varying cross-sectional dimensions.

58. A contraceptive as recited in claim 57 wherein said discontinuity is from 15 to 33⅓ percent of the circumferential length of said rim.

59. A contraceptive as recited in claim 58 wherein said rim means comprises a substantially annular member defining a substantially circular configuration; said discontinuity being defined by spaced ends of said annular member, said annular member being resilient such that said ends may be pressed together to thereby reduce the diameter of said rim means.

60. A contraceptive as recited in claim 59 wherein said free ends being rounded.

61. A contraceptive as recited in claim 58 wherein said rim means comprises a substantially annular member defining a substantially circular configuration; said discontinuity being defined by overlapping separate ends of said annular member, said annular member being resilient such that said ends may be free to move about said circumference of said rim to thereby reduce the diameter of said rim means.

62. A contraceptive as recited in claim 61 wherein said free ends being rounded.

63. A contraceptive as recited in claim 58 wherein said rim means comprises a generally continuous, discoidal, resilient member having a notch in one circumferential part thereof; and an envelope of a flexible member having a discoidal shape for enclosing said discoidal resilient member; said notched ends being so spaced such that, upon pushing said notched ends together, the diameter of said rim means being reduced.

64. A contraceptive as recited in claim 63 wherein said notch comprising a segment of a circle.

65. A barrier contraceptive of the type intended to be inserted within a vaginal vault, said contraceptive comprising:

(a) a first member having opposed anterior and posterior portions and having lateral portions for releasably and resiliently engaging the lateral portions of the vaginal vault; and
(b) a second member coupled to said first member substantially at said posterior portion, such that, upon insertion of said contraceptive into the vaginal vault with said second member disposed between said first member and the cervix and said first member lateral portions engaging the lateral portions of the vault, said second member being positionable to thereby close the cervical opening and is so dimensioned as to be substantially removed from contact from the vaginal vault; said first member buffers said second member from the effects of the forces of the vaginal vault to thereby substantially maintain said second member in position.

66. A contraceptive as recited in claim 65 wherein said first and second members each having substantially discoid configurations and said second member having a smaller disc surface area than said first member.

67. A contraceptive as recited in claim 66 wherein said second member comprises a sponge-like material, said sponge material being capable of receiving a lubricant.

68. A contraceptive as recited in claim 67 wherein said second member being resiliently secured to said first member for movement away from said first member so as to yieldably contact and close the cervical opening.

69. A barrier contraceptive as recited in claim 68 wherein said first member comprises a continuous annular rim.

70. A barrier contraceptive as recited in claim 69 wherein said annular rim defining the perimeter of a circle and further defining diametrically opposed substantially obtuse partial segments of said circle; the diameter intersecting the juncture of said partial segments substantially intersecting said anterior and posterior portions of said first member.

71. A barrier contraceptive as recited in claim 70 further comprises a soft, pliable, sponge-like, plastic material enveloping said rim and conforming to said annular shape.

72. A barrier contraceptive as recited in claim 71 wherein said second member comprises said plastic material being continuous with said envelope.

73. A barrier contraceptive as recited in claim 72 wherein said first and second members being substantially defined by a sandwich of said plastic, said rim being sealed within said first member, said rim having an outer diameter in an approximate range of 60 to 85 mm, said obtuse segments being separated by a chord within an approximate range of 20 to 40 mm, said partial segment extending radially inwardly from the circumference of said rim in an approximate range of 15 to 25 mm, the apex of said inwardmost extension being in an approximate range of 15 to 25 mm, said rim having a cross-sectional diameter in an approximate range of 2.3 to 3.0 mm, the innermost points of said rim being disposed above said annular portion in an approximate range of 6 to 10 mm and having a radius of curvature of approximately 5 mm, said second member having a diameter of approximately 40 mm.

74. A barrier contraceptive as recited in claim 70 wherein said partial segments extending inwardly of said outer circumference of said rim for a part of the radii of said annulus; the apexes of said inward extensions being disposed at an acute angle above a plane defined by said annular portion of said obtuse segments, to thereby form a dome-shaped member.

75. A barrier contraceptive as recited in claim 71 wherein said partial segments extending inwardly of said outer circumference of said rim for a part of the radii of said annulus; the apexes of said inward extensions being disposed at an acute angle above a plane defined by said annular portion of said obtuse segments, to thereby form a dome-shaped member.

76. A contraceptive as recited in claim 72 further comprises a lubricant, said second member being moistened by said lubricant to thereby aid in closing said cervix; said second member being impermeable.

77. A contraceptive as recited in claim 76 wherein said lubricant further comprises adhesive properties so as to thereby aid in the adhesion of said second member upon being disposed against the cervix.

78. A contraceptive as recited in claim 72 wherein said first member being lubricated.

79. A contraceptive as recited in claim 77 wherein said first member being lubricated.

80. A contraceptive as recited in claim 44 wherein said resilient and flexible means comprises an annular rim defining diametrically opposed substantially obtuse partial segments of a circle; the diameter intersecting the juncture of said partial segments substantially intersecting said anterior and posterior portions of said first member; said cervix engaging means comprises a substantially discoid sponge-like member integrally formed with said resilient and flexible means.

81. A contraceptive as recited in claim 80 wherein said rim having posterior and anterior portions; said rim portions being for alignment with the corresponding posterior and anterior portions of the vaginal vault; said rim having lateral portions for resiliently and releasably engaging the respective lateral walls of the vaginal vault and wherein said partial segments extending inwardly of said outer circumference of said rim for a part of the radii of said annulus; the apexes of said inward extensions being disposed at an acute angle above a plane defined by said annular portion of said obtuse segments, to thereby form a dome-shaped member.

82. A contraceptive as recited in claim 65 wherein said second member being hingeably joined to said first member, said first member being resilently foldable along a line from said posterior to said anterior portion, thereby urging said second member into engagement with the cervix, said first member opening from said foldable position along said line to be engageable with the lateral wall of the vaginal vault.

83. A contraceptive as recited in claim 70 wherein said second member being hingeably joined to said first member, said first member being resiliently foldably along a line from said posterior to said anterior portion, thereby urging said second member into engagement with the cervix, said first member opening from said foldable position along said line to be engageable with the lateral wall of the vaginal vault.

84. A contraceptive as recited in claim 78 wherein said second member being hingeably joined to said first member, said first member being resiliently foldable along a line from said posterior to said anterior portion, thereby urging said second member into engagement with the cervix, said first member opening from said foldable position along said line to be engageable with the lateral wall of the vaginal vault.

85. A contraceptive as recited in claim 79 wherein said second member being hingeably joined to said first member, said first member being resiliently foldable along a line from said posterior to said anterior portion, thereby urging said second member into engagement with the cervix, said first member opening from said foldable position along said line to be engageable with the lateral wall of the vaginal vault.

86. A female contraceptive for use in a vaginal vault and acting as a barrier for blocking the entry of foreign matter into a cervix; said contraceptive comprising:
    (a) member means for providing the barrier; and
    (b) rim means for engaging the wall of the vault and being in cooperative engagement with said member means; said rim means being resiliently and flexibly foldable along a predetermined diameter thereof, so as to be engageable with the vaginal vault positioning said contraceptive, said flexibility and resiliency enabling said rim means to be received and accommodated by vaginal vaults of varying cross-sectional dimensions.

87. A female contraceptive as recited in claim 86 wherein said rim comprises a continuous member defining at least two obtuse partial segments of a circle conjoined at said diameter and covered with a soft material.

88. A female contraceptive as recited in claim 87 wherein said partial segments being defined by said rim defining therebetween substantially equal acute angles diametrically opposed to one another with the apexes thereof co-linear with said diameter.

89. A female contraceptive as recited in claim 88 wherein said covering of said rim being substantially a first discoid, said opposed acute angles being disposed to come into alignment with the anterior and posterior portions of the vaginal vault; respectively.

90. A female contraceptive as recited in claim 88 wherein said member barrier means being substantially a second discoid and integrally formed and hingedly joined at said posterior portion of said covering rim and foldable over, so as to be substantially within a plane parallel to said first discoid and so as to be hingedly moved from said plane by said folding of said first discoid along said diameter, thereby being capable of engaging the cervix.

91. A contraceptive as recited in claim 65 wherein said first member being substantially within a plane and being resiliently foldable along a line from said anterior to said posterior portions, said line being co-planar with said plane, said folding of said first member thereby urging said second member into contact with the cervical opening.

92. A contraceptive as recited in claim 90 wherein said first and second members each having a substantially discoid configuration, said first member having a rim therein defined by conjoined obtuse partial segments, said segments being joined by said line and defining therebetween acute angles, the apexes of said acute angles being spaced from one another and disposed at an acute angle with respect to said plane, a soft, sponge-like discoid covering enclosing said rim, said apexes providing a dome-like configuration.

* * * * *